United States Patent [19]

Fu et al.

[11] 4,431,936

[45] Feb. 14, 1984

[54] TRANSDUCER STRUCTURE FOR GENERATING UNIFORM AND FOCUSED ULTRASONIC BEAMS AND APPLICATIONS THEREOF

[75] Inventors: Chong-Cheng Fu, Stanford; Levy Gerzberg, Palo Alto, both of Calif.

[73] Assignee: The Board of Trustees of the Leland Stanford Junior University, Stanford, Calif.

[21] Appl. No.: 350,020

[22] Filed: Feb. 18, 1982

[51] Int. Cl.³ .............................................. H01L 41/04
[52] U.S. Cl. ................................. 310/335; 73/861.25; 128/663; 310/369
[58] Field of Search ............... 310/337, 334, 335, 369; 128/660, 663, 661; 73/642, 861.25; 367/150, 164; 343/854; 316/322, 366

[56] References Cited

U.S. PATENT DOCUMENTS

| 3,327,286 | 6/1967 | Dorr et al. | 367/155 |
| 3,888,238 | 6/1975 | Meindl et al. | 128/2 V |
| 4,051,455 | 9/1977 | Fowler | 340/9 |
| 4,062,237 | 12/1977 | Fox | 73/194 A |
| 4,228,687 | 10/1980 | Fraser | 73/626 |

OTHER PUBLICATIONS

Fu, C., et al., "Annular Arrays for Quantitative Pulsed-Doppler Ultrasonic Flowmeters", Ultrasonic Imaging, vol. 5, 1983, pp. 1-16.
Hottinger and Meindl, "Blood Flow Measurement Using the Attenuation-Compensated Volume Flow Meter", *Ultrasonic Imaging*, vol. No. 1, 1979.
Defranould, P., et al. "Design of a Two Dimensional Array for B and C Ultrasonic Imaging System", 1977 *Ultrasonics Symposium Proceedings*, IEEE Cat. 11 77 CH 1264-ISU, pp. 259-263.

*Primary Examiner*—J. D. Miller
*Assistant Examiner*—D. L. Rebsch
*Attorney, Agent, or Firm*—Flehr, Hohbach, Test, Albritton & Herbert

[57] ABSTRACT

Transducer structures for use in volume flow measurements which generate a first uniform beam and a second focused beam within the uniform beam. The transducer may include concentric elements, a linear array, or combinations thereof. In a two element concentric array, a central disc generates a uniform beam and a peripheral annular element having a lens thereon defines a second focused beam within the first beam. In a linear array, a plurality of juxtaposed linear elements define a scan surface, and a segmented element within the linear element array defines a focused reference sample volume within the scanned surface. A concentric array having a plurality of annular elements is driven with amplitude weighting of each element, in accordance with a Fourier-Bessel approximation to the desired beam pattern, thereby electronically achieving ultrasonic beam width control.

6 Claims, 13 Drawing Figures

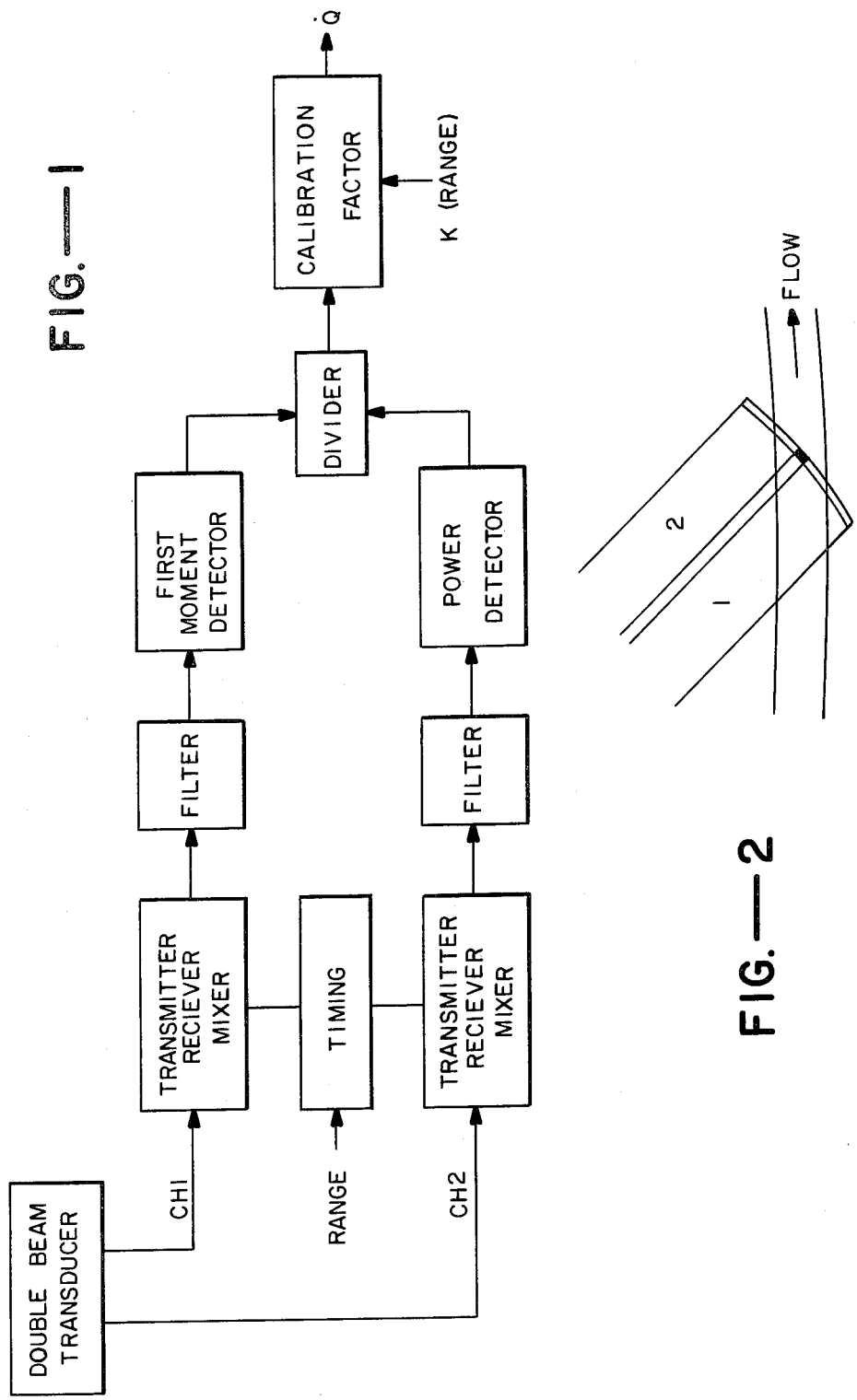

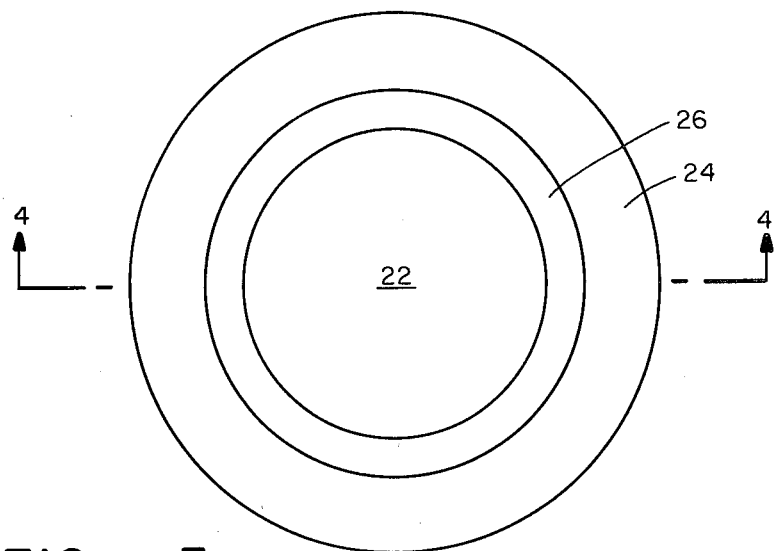
FIG.—3
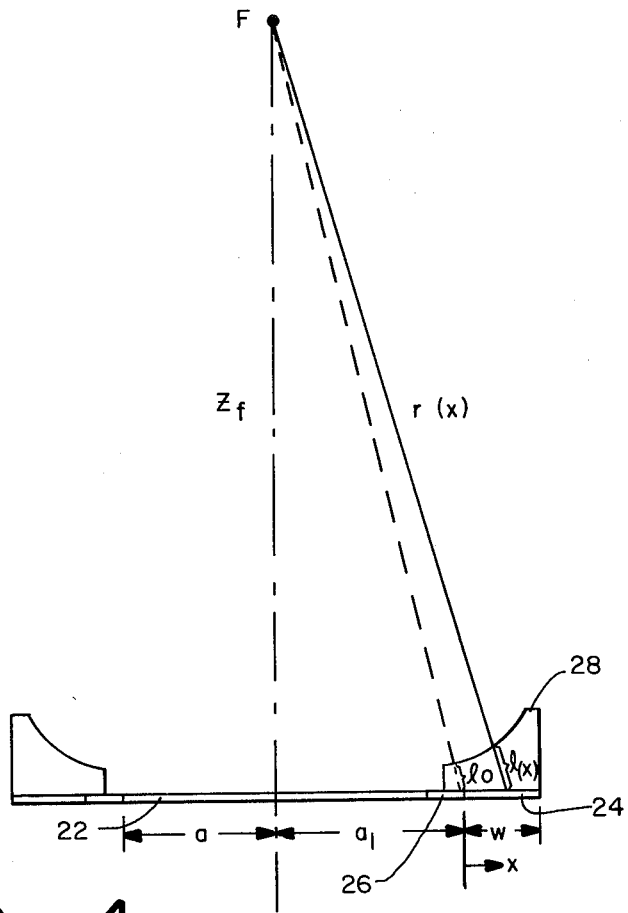
FIG.—4

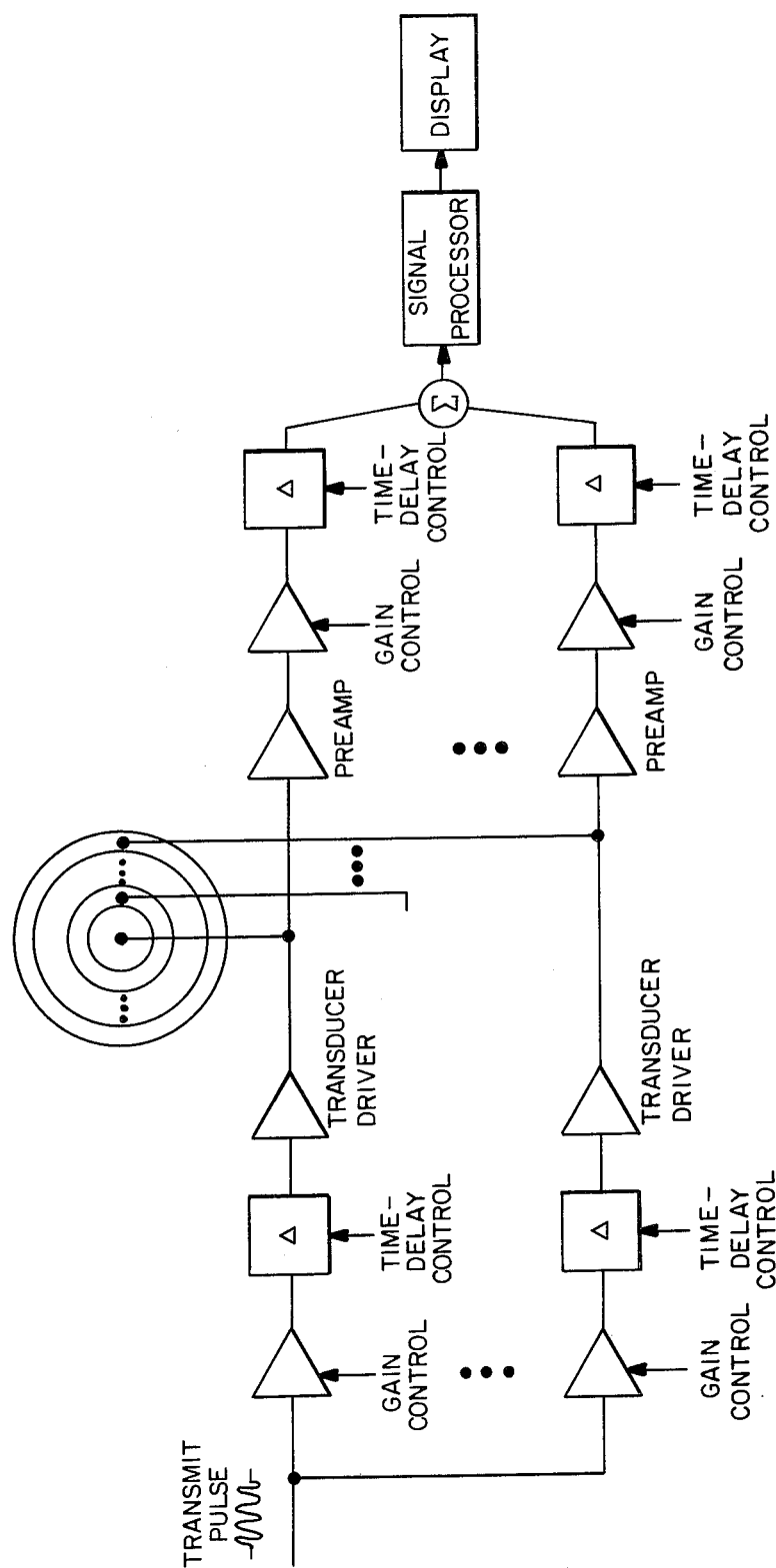
FIG.—5

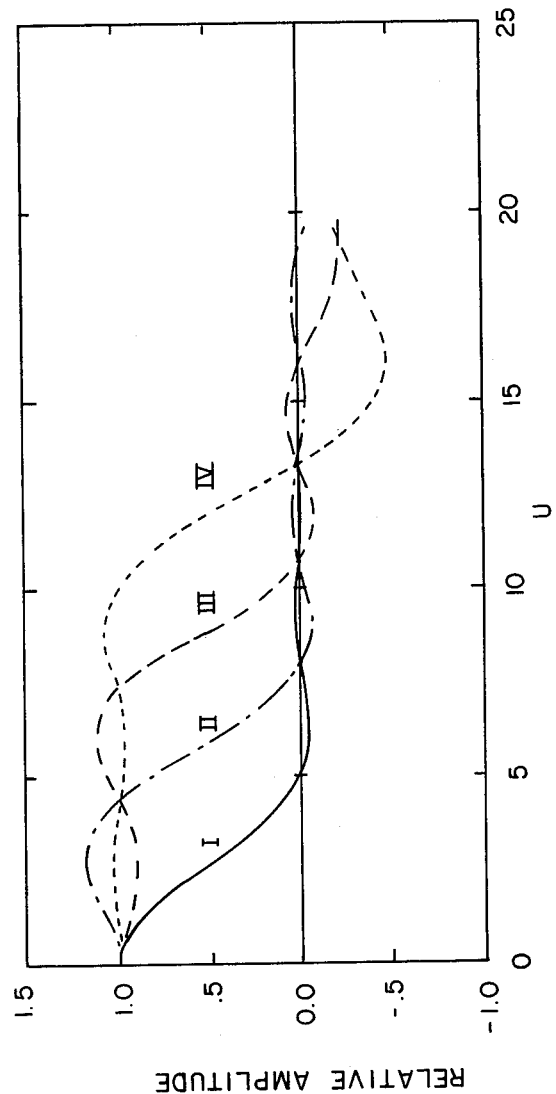
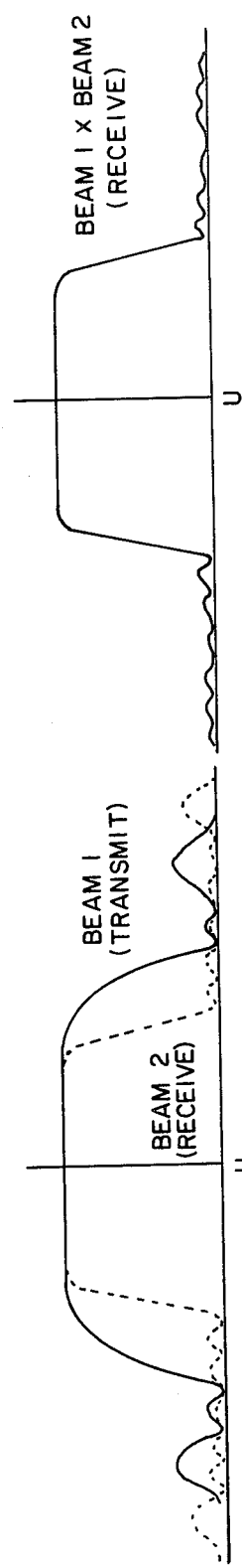
FIG.—6
FIG.—7a
FIG.—7b

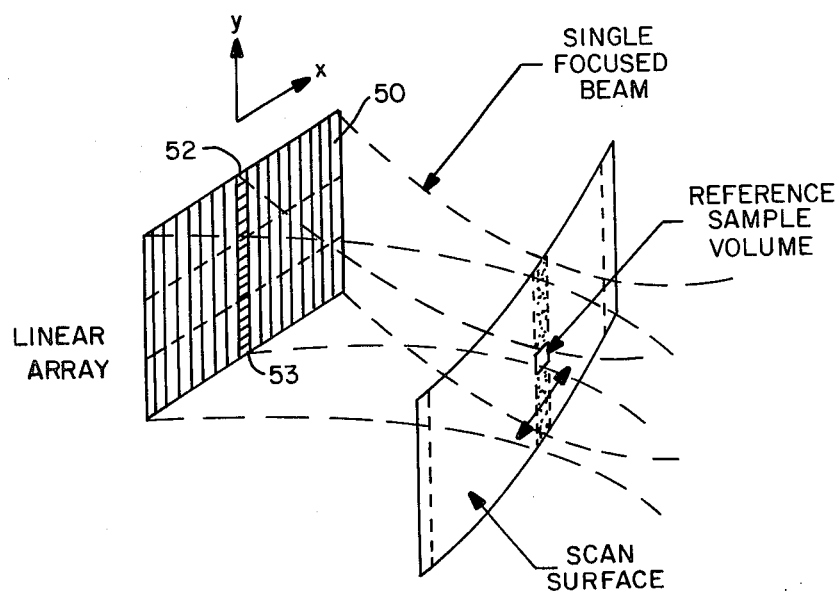
FIG.—8
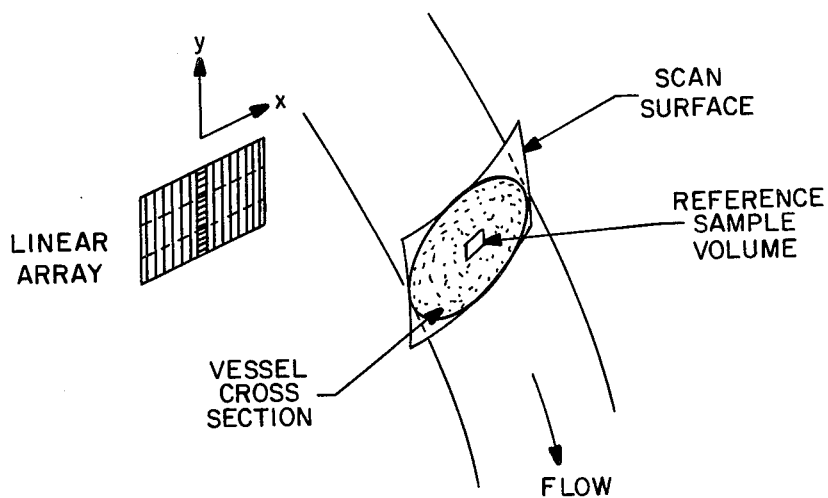
FIG.—9

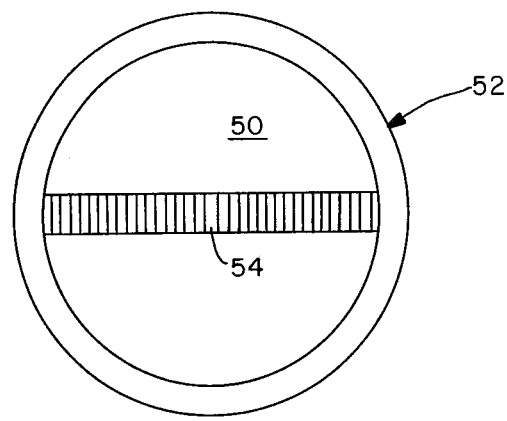
FIG.—10a
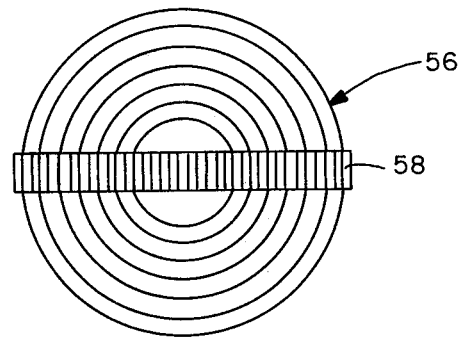
FIG.—10b
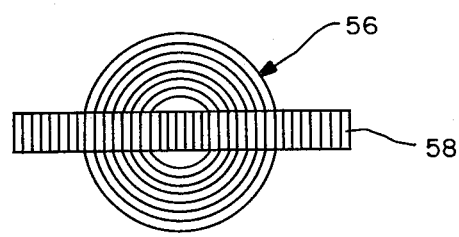
FIG.—10c

TRANSDUCER STRUCTURE FOR GENERATING UNIFORM AND FOCUSED ULTRASONIC BEAMS AND APPLICATIONS THEREOF

This invention relates generally to ultrasonic transducers, and more particularly the invention relates to such transducers for use in measuring blood volume flow and like measurements and for imaging applications.

Doppler ultrasound has been recognized as a potential approach to the non-invasive measurement of blood flow. However, this method has not become a quantitative clinical tool because existing Doppler instruments estimate volume flow as a product of the velocity of blood and vessel cross sectional area. This requires accurate measurement of the three-dimensional velocity-vector orientation with respect to the ultrasonic beam plus an independent measurement of lumen cross sectional area. Difficulties associated with the accurate determination of these variables have heretofore restricted all non-invasive applications of Doppler flowmeters to qualitative measurements.

A novel concept for quantitative non-invasive Doppler blood flow measurement is disclosed by Hottinger and Meindl in "Blood Flow Measurement Using the Attenuation-Compensated Volume Flow Meter" *Ultrasonic Imaging*, Vol. 1, No. 1, 1979. See U.S. Pat. No. 3,888,238 for "Blood Flow Measuring Apparatus". This concept is based on a direct flow-rate estimation rather than on separate velocity and cross sectional area measurements and does not rely on precise knowledge of these parameters. The method does require a uniform ultrasonic illumination of the vascular lumen cross section and the positioning of a second small sampling beam inside the vessel. Thus, ultrasonic transducers are required for uniform illumination of the entire vessel cross section area and simultaneous focused illumination with range and beam width control.

Heretofore ultrasonic transducers for realizing the requisite ultrasonic beam patterns have included a far-field approach in which a uniform field is provided by a diverging beam in the far field of a small transducer. A near-field approach utilizes a transducer composed of two co-planar elements including a small central element and a large circumferential element. The two elements are driven simultaneously and equally to simulate a single transducer and thus provide a uniform insonification. In the receive mode, the small element receives a signal from the reference sample volume while the signals received by both elements are summed to collect the signal returning from the whole vessel cross section. In a lens approach a diverging lens is positioned over a small central transducer element to generate a diverging beam that is uniform over a specified solid angle, and a converging lens is placed over an annular element to produce a slightly converging beam.

These known approaches are all limited in their applications to blood flow measurement primarily because their beam patterns are fixed by the geometric configurations of the transducers. In addition, each approach has its own difficulties or limitations. For example, in the far-field approach the uniform beam patterns are difficult to obtain. For a circular shaped transducer as an example, continuous-wave diffraction theory requires that the driving function be a continuous spatial distribution which has been difficult to achieve by any practical means. In the lens approach, diffraction usually makes generation of a uniform beam profile very difficult. Additionally, high precision is required in the lens construction. The near-field approach is simpler and more practical, but the summation of signals of two elements still requires very close inter-element matching in transducer characteristics and in the associated control circuitry.

Accordingly, an object of the present invention is improved transducers for use in ultrasonic flow measurement.

Another object of the invention is an improved transducer for use in near and far field applications.

A further object of the invention is an improved method of ultrasonic wave transmission using a circular transducer array with adjustable beam widths.

Yet another object of the invention is a phased array transducer having electronically adjustable beam width and uniform cross section and which can selectively receive a small reference area from within the beam cross section.

Still another object of the invention is a combination of scanning transducer and flow-measuring transducer.

The invention and objects and features thereof will be more readily apparent from the following detailed description and appended claims when taken with the drawing, in which:

FIG. 1 is a functional block diagram of a quantitative Doppler flow meter which employs transducers in accordance with the present invention.

FIG. 2 illustrates requisite ultrasonic beams of transducers in accordance with the present invention.

FIG. 3 is a top view of a two element transducer in accordance with the present invention.

FIG. 4 is a section view of the two element transducer of FIG. 3 taken along the line 4—4.

FIG. 5 is a functional block diagram illustrating the operation of a concentric transducer array in accordance with the invention.

FIG. 6 is a plot of signal patterns generated by an annular array.

FIGS. 7a and 7b illustrate a method of sidelobe suppression using an annular array in accordance with the invention.

FIG. 8 is a perspective view of a linear transducer array in accordance with the invention illustrating the establishment of a reference sample volume.

FIG. 9 illustrates the application of the transducer array of FIG. 8 in an attenuation-compensated flow meter.

FIGS. 10a–10c illustrate combinations of transducers for both imaging and flow measurements in accordance with the invention.

Referring now to the drawings, FIG. 1 is a functional block diagram of the attenuation-compensated volume flow meter as described by Hottinger and Meindl, supra. The flow meter employs a double beam pulsed Doppler transducer which uniformly illuminates a vessel. The array generates repeated short bursts of ultrasound, and the signals returning to the transducer are simultaneously range gated and processed to create two thin sample volumes, as illustrated in the drawing of FIG. 2 which illustrates the waves intersecting a vessel. As shown in FIG. 2, volume 1 constitutes a large uniformly illuminated sample plane covering the entire lumen cross section of the vessel. The second volume is a small disc which is a part of the larger plane and lies totally within the lumen.

As described by Hottinger and Meindl, the two Doppler audio signals are produced by the Transmitter/Receiver circuitry of FIG. 1. The received signals are transmitted through filters to a first-moment detector and a power detector. The filters compensate for sampling effects arising from the pulse nature of the waveforms, and the outputs of the circuitry are the Doppler spectra of beams one and two. A range dependent scale factor (K) is introduced at the output. The flow rate $\dot{Q}$ at the output is expressed in terms of the measurable parameters and is defined by the first moment of the Doppler power spectrum received in beam one and normalized by the power received in beam 2.

FIG. 3 is a plan view of a two element transducer in accordance with the present invention useful in the system of FIG. 1, and FIG. 4 is a section view of the transducer of FIG. 3 taken along the line 4—4. The transducer includes a first central disc shaped element 22 and an annular transducer element 24 which surrounds the disc shaped element. The two elements are insulated from each other by insulation 26 such as delrin. As shown in FIG. 4, a concave surface lens 28 is bonded to the annular transducer element 24. In operation, an ultrasonic wave is generated solely by the disc transducer 22, and the annular transducer 24 is used only in the receive mode to obtain a signal from the sample volume located on the transducer axis. The lens is capable of sufficient on-axis focusing over a finite range around the specified focal point, and by using a range gate, the depth of the sample volume can be varied.

The transducers are made of suitable piezoelectric ceramics and have a thickness on the order of one-half the operating frequency wavelength. For example, for a six megahertz ultrasonic wavelength, the thickness is on the order of 0.37 millimeters. The lens is made of a material such as lucite or nylon which has suitable acoustic refractive indices. The lens geometry is determined based on the criterion that acoustic waves originating from a specified on-axis focal point should arrive simultaneously at all points on the annular transducer surface. Referring to FIG. 4 and assuming that refraction at the lens surface can be neglected, this criterion requires that $$\frac{l(x)}{c_2} + \frac{r(x) - l(x)}{c_1} = T \text{ for } 0 \leq x \leq w, \quad (1)$$

where $$r(x) = \sqrt{z_f^2 + (a_1 + x)^2}$$

is the distance between the focal point F at the focal distance $z_f$ and a point x on the annular transducer, $x=0$ being set at the inner edge of the transducer, $l(x)$ is the path length in the lens, T is the constant total propagation time, and $c_1$ and $c_2$ are acoustic velocities in body tissues and the lens material, respectively. In this design, we take $c_1=1500$ m/sec and $c_2=2650$ m/sec, and hence the refractive index of the lens $n=c_1/c_2\approx 0.56$.

$l(x)$ can be obtained from Eq. (1) as $$l(x) = \frac{r(x) - c_1 T}{1 - n} \quad (2)$$

Let $l_o = l(0)$; it follows that $$T = \frac{1}{c_1} [\sqrt{z_f^2 + a_1^2} - (1 - n)l_o], \quad (3)$$

and hence $$l(x) = l_o + \frac{1}{1 - n} [\sqrt{z_f^2 + (a_1 + x)^2} - \sqrt{z_f^2 + a_1^2}]. \quad (4)$$

For simplicity of system implementation it is desirable that T be equal to the propagation time to the disk element from the same range, that is $$T = \frac{z_f}{c_1}. \quad (5)$$

Combining equations (3) and (5), we have $$l_o = \frac{\sqrt{z_f^2 + a_1^2} - z_f}{1 - n}, \quad (6)$$

which, in conjunction with Eq. (2), determines the lens geometry given the value of n. For a narrow annular transducer element, the assumption of negligible refraction is usually acceptable. For example, in the case that $z_f=3$ cm, $a_1=7$ mm and $w=2$ mm, the incident angle at the lens surface determined as above can be shown to be no greater than 15°.

FIG. 5 is a functional block diagram of an attenuation-compensated volume flow meter which employs a concentric transducer array consisting of a center disc element and a plurality of concentric annular elements. Such a transducer array is disclosed by Dietz et al in "Expanded-Aperture Annular Array", *Ultrasonic Imaging*, One, 1979, pgs. 56–75. In accordance with the invention, the annular transducer array generates a uniform sector pattern by operating the individual annular elements with independent amplitude and timing controls. More particularly, the beam pattern synthesis using the array is based on a Fourier-Bessel approximation to the desired beam pattern.

Let $r_1, r_2, \ldots, r_N$, where N is the total number of elements, be the outer radii of the elements (FIG. 3), and $a_1, a_2, \ldots, a_N$ the amplitudes of the driving signals. Then the far-field diffraction pattern of this array can be expressed as $$f(u) = a_1 r_1 \frac{J_1(r_1 u)}{u} + a_2 \left\{ r_2 \frac{J_1(r_2 u)}{u} - r_1 \frac{J_1(r_1 u)}{u} \right\} + \quad (7)$$

$$a_N \left\{ r_N \frac{J_1(r_N u)}{u} - r_{N-1} \frac{J_1(r_{N-1} u)}{u} \right\}$$

$$\text{or } f(u) = \sum_{n=1}^{N} (a_n - a_{n+1}) r_n \frac{J_1(r_n u)}{u},$$

with $a_{N+1}=0$ and $u=(2\pi/\lambda) \sin \theta$, where $\theta$ is the field direction with respect to the array axis, and $\lambda$ is the signal wavelength.

Suppose the radii are proportional to the positive zeroes $\alpha_1, \alpha_2, \ldots, \alpha_N$ of $J_1(x)$, and let $r_n=b\alpha_n$, then Eq. (7) can be rewritten as $$u \cdot f(u) = \sum_{n=1}^{N} (a_n - a_{n+1}) b a_n J_1(b a_n u), \quad (8)$$

or $$v \cdot f\left(\frac{v}{b}\right) = \sum_{n=1}^{N} b^2 (a_n - a_{n+1}) a_n J_1(a_n v),$$

with $v = bu$.

Fourier-Bessel series expansion theorem states that an arbitrary function g(x) can be expanded in the interval (0,1) as $$g(x) = \sum_{n=1}^{\infty} s_n J_1(\alpha_n x) \quad (9)$$

and the coefficients $\{s_n\}$ are given by $$s_n = \frac{2}{J_2^2(\alpha_n)} \int_0^\infty t g(t) J_1(\alpha_n t) dt. \quad (10)$$

Based on the similarity in form between equations (8) and (9), the beam pattern synthesis scheme can be designed according to the following procedure:

(1) Given a desired circularly symmetrical beam pattern $f_o(u)$ introduce a new function $g_o(v)$ such that $$g_o(v) = v \cdot f_o\left(\frac{v}{b}\right)$$

and $0 \leq bu \leq 1$ over the extent of $f_o(u)$.

(2) Calculate $$s_n = \frac{2}{J_2^2(\alpha_n)} \int_0^1 t g_o(t) J_1(\alpha_n t) dt.$$

(3) Calculate $\{a_n\}$ iteratively according to the relation $$s_n = b^2 \alpha_n (a_n - a_{n+1})$$

and $$a_{N+1} = 0.$$

Thus, a set of amplitude weightings is obtained which upon application to the annular array will generate an approximation to the desired beam pattern. As the number of elements N increases, the approximation becomes closer.

When this technique is used to form the uniform beam pattern, patterns of various beam widths can be obtained with a given array configuration. Analysis shows that N different patterns, each approximating a uniform sector pattern, can be generated with an N-element annular array. A narrow focused beam and a rather wide and uniform field can be obtained in the far field of a multiannulus array by correctly designing the signal-amplitude weightings on the array elements. Combined with the dynamic focusing capability of the ultrasonic transducer array, these features can also be extended to the near field. The beam patterns generated by this method with a four-element array are shown in FIG. 6.

In an implementation of the annular array, in accordance with the invention, the blood vessel can be interrogated alternately by the wide beam and narrow beam from the same array, thereby producing the signals for the two different channels. When a higher pulse repetition rate is necessary to avoid velocity ambiguity at a given range, one can transmit one narrow beam after every several uniform beams because the information contained in the small sample volume presumably does not need to be sampled as fast as the other channel. One can also insonify the vessel cross section with the wide beam while receiving signals at both channels simultaneously by two independent weighted coherent summations which can double the effective sampling rate.

The major advantages of this approach are twofold in that the beamwidth can be varied to match the size of the blood vessel, and because it is easy to control the operating range, this method is applicable to both superficial and deep-lying vessels.

Another important feature of this embodiment of the invention is suppression of the sidelobe level outside the region of the uniform field, which may insonify undesirable regions outside the blood vessel being investigated (for example, another vessel nearby). As illustrated in FIGS. 7a and 7b this problem can be solved by using a first beam having a first beam width for transmit mode and two different width beams for receive mode. The two received beams are amplitude weighted with respect to the transmitted beam whereby sidelobe suppression is achieved as illustrated in FIG. 7b for Beam 1 (transmit) and Beam 2 (receive). This process can be accomplished in the circuitry of FIG. 5 for example where each annular element is individually weighted. The second and third beams are obtained by summing two sets, respectively, of individually weighted signal components from each of the annular elements so that their sidelobes do not overlap with the sidelobes of Beam 1, thereby minimizing the sidelobe effect.

FIG. 8 is a perspective view of a linear phased array transducer in accordance with another embodiment of the invention. The array comprises a plurality of long and narrow elements 50 in planar juxtaposition and a centrally disposed element 52 which comprises a plurality of individual segments 53. Each of the elements and segments have electrical connections for energizing the elements and receiving signals from the segments. As illustrated in FIG. 8 the linear elements 50 can be electronically steered across a scan surface, and the segments 53 of the element 52 can be steered to focus on the reference sample volume as indicated. Thus, the linear phased array has the unique capability of electronically steering the beam in one lateral dimension in addition to dynamical focusing. The extent of beam steering can be controlled by the operator, making it possible to synthesize a variable sized surface and adjust the size as required for each specific application. The coverage of the other lateral dimension, however, is fixed by the array dimension and cannot be controlled by a simple one dimensional linear array; the array must have sufficient width so that the resultant two dimensional surface can cover the entire vessel cross section.

FIG. 9 illustrates one implementation wherein the beam is focused in the X dimension and is sufficiently wide in the Y dimension to cover the vessel cross section. In the transmit mode a wide illumination is created by exciting either the whole rectangular array or only a few elements in the center. In the receive mode, signals from all directions of interest are extracted at the same time by a suitable set of delay lines. The segments 53 in element 52 provide the additional focusing in the Y dimension as required in the central region of the scan surface to generate the reference sample volume which is the overlap of the two focus beams.

Alternative embodiments of transducers in accordance with the invention may comprise combinations of scanning transducers and flow measuring transducers as described above. For example, FIG. 10a employs a split disc 50 for the uniform beam and a focused annulus 52 and the imaging linear array 54. Alternatively, as shown in FIGS. 10b and 10c, an annular array shown generally at 56 can be used to provide the beam width control capability in combination with the imaging linear array 58.

A plurality of transducer embodiments have been described which allow uniform illumination of a vessel and signal reception from a small reference volume completely within the illuminated vessel. While the invention has been described with reference to specific embodiments, the description is illustrative of the invention and is not to be construed as limiting the invention. Various modifications and applications may occur to those skilled in the art without departing from the true spirit and scope of the invention as defined by the appended claims.

What is claimed is:

1. A transducer structure for use in ultrasonic flow measurements comprising a first planar disc-shaped transducer element for generating and receiving a first uniform ultrasonic beam, a second annular transducer element about said first transducer element, and lens means on one surface of said second transducer element for receiving a second ultrasonic beam which is focused within said first beam.

2. The transducer structure as defined by claim 1 and further including insulation between said first and second transducer elements.

3. The transducer structure as defined by claim 1 or 2 wherein the thickness of said first transducer element is on the order of one-half an ultrasonic operating frequency wavelength.

4. A transducer structure for use in ultrasonic flow measurements and like applications where uniform and focused beams are required comprising a plurality of concentric transducer elements, a central element of said plurality of transducer elements being a disc, an outer element of said plurality of transducer elements including a lens for defining said focused beam, and a linear array of elements centrally disposed through said plurality of transducer elements, said plurality of concentric elements generating a first uniform beam and a second narrow beam and said linear array generating a scan beam for imaging.

5. A transducer structure for use in ultrasonic flow measurements and like applications where uniform and focused beams are required comprising a plurality of concentric transducer elements, said plurality of transducer elements being selectively energizable to define a focused beam, a central element of said plurality of transducer elements being a disc, and a linear array of elements centrally disposed through said plurality of transducer elements, said plurality of concentric elements generating a first uniform beam and a second narrow beam and said linear array generating a scan beam for imaging.

6. The transducer structure as defined by claim 4 or 5 wherein each concentric transducer element is amplitude weighted in accordance with the equation $$S_n = b^2 a_n (a_n - a_{n+1})$$

where
$a_1, a_2, \ldots, a_n$ is the amplitude of the driving signals
$r_1, r_2 \ldots, r_N$ are the radii of the elements from the center outward
N is the number of elements
$\alpha_1, \alpha_2, \ldots, \alpha_N$ are positive zeroes of the Bessel function $J_1(x)$
$b = r_n/\alpha_n$ and $$S_n = \frac{2}{J_2^2(\alpha_n)} \int_0^1 t\, g_o(t) J_1(\alpha_n t)\, dt.$$

where
t is integration variable
$g_o(\cdot)$ is defined by $g_o(v) = v \cdot f_o(v/b)$
$f_o(u)$ is the desired beam pattern
where
u is $(2\pi/\lambda) \sin \theta$, and $\theta$ is the field direction.

* * * * *

UNITED STATES PATENT AND TRADEMARK OFFICE
CERTIFICATE OF CORRECTION

PATENT NO. : 4,431,936
DATED : February 14, 1984
INVENTOR(S) : Chong-Cheng Fu et al.

It is certified that error appears in the above-indentified patent and that said Letters Patent is hereby corrected as shown below:

Column 1, line 5, insert the following information:

--This invention was made with Government support under contract No. GM17940 awarded by Health and Human Services. The Government has certain rights in this invention.--

Signed and Sealed this

Sixth Day of December, 1994

Attest:

BRUCE LEHMAN

*Attesting Officer*            *Commissioner of Patents and Trademarks*